April 20, 1971 W. PENNOCK Plant Pat. 3,050
AVOCADO
Filed March 5, 1969
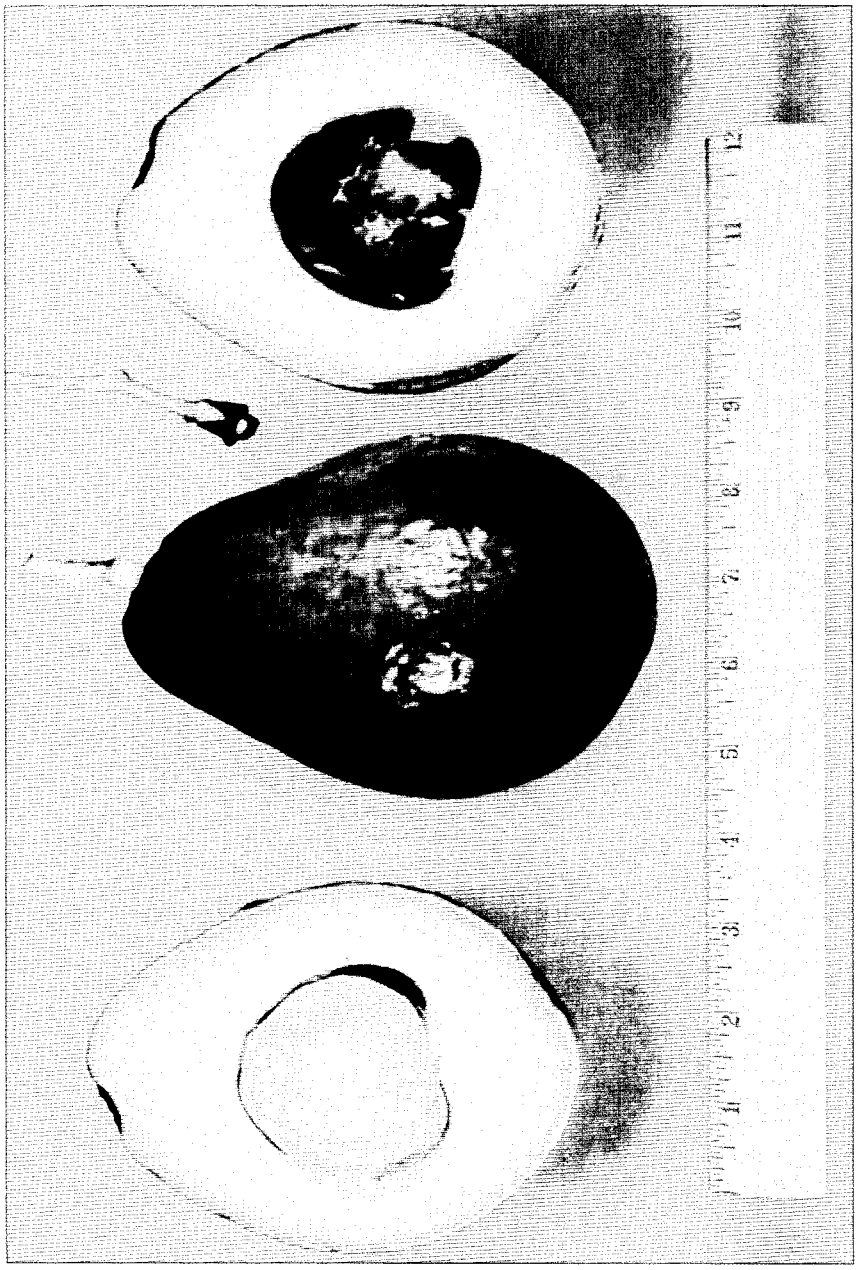

United States Patent Office

Plant Pat. 3,050
Patented Apr. 20, 1971

3,050

AVOCADO

William Pennock, Toa Baja, Puerto Rico, assignor to Commonwealth of Puerto Rico, as the representative of all of the people of Puerto Rico Filed Mar. 5, 1969, Ser. No. 804,720
Int. Cl. A01h 5/03
U.S. Cl. Plt.—44 1 Claim

ABSTRACT OF THE DISCLOSURE

The original tree is a hybrid seedling having Guatemalan and West Indian parentage. The clove was propagated asexually. The tree is a prolific bearer having characteristics favorable to production and transportation.

This invention relates to a new and improved variety of avacado, having many desirable characteristics as will appear hereinafter.

The actual parentage of the avocado is not known precisely. It originated as a volunteer seedling in Finca El Semil, a farm located near the town of Villalba, Puerto Rico. Its characteristics such as color of foliage, size and shape of pedicle, its bearing season, its oil content, its tight seed and its pliable yet thick skin are all suggestive of hybrid origin involving the Guatemalan race on the one hand and the West Indian race on the other. At Finca El Semil a collection of Guatemalan varieties introduced by the United States Department of Agriculture had been set out many years ago in an area where many West Indian seedling trees were already present. The clone was propagated asexually by applicant.

The tree is typical of avocado trees, being upright in form, vigorous in growth and spreading in nature, its habit being similar in many respects to the Collison variety. The foliage is abundant and fairly compact. The leaves are from 6.5 to 9 inches in length and from 3.5 to 4 inches in width, having a petiole 1.5 to 1.66 inches long. The color is dark green. The leaf shape is elliptical with cuspidate apex and a slight attenuated to cuneate base. The tree is vigorous and a regular and prolific bearer. One outstanding characteristic is its ability to hold the fruit in high winds. Another characteristic is its high refrigeration tolerance, with an Index of 412.

The flower is designated as Type A in which all open flowers are female functional in the forenoon and male functional in the afternoon.

The fruit is harvested between November 15 and February 15.

The fruit depends from a practically vertical stem. The receptacle is medium-small and conico-cylindrical in shape with a slight flange-like disc. This results in the ability of the fruit to remain on the stem under adverse weather conditions.

The length of the entire avocado fruit stem depends mostly on the position of the flower from which it evolved in the inflorescence. If it is near the base of the inflorescence the stem will be short; if near the end it will be long. For this reason when attempting to distinguish between varieties we describe the fleshy first joint of the stem which is derived from the receptacle of the flower. In the case of the present variety, which has been designated Semil 34 by the Commonwealth of Puerto Rico, the receptacle is conico-cylindrical in shape and medium small being about ⅜ inch long and about ⅜ inch in diameter at its thickest part where it touches the fruit. The attachment of the button to the stem and of the stem to the tree is strong so that relatively high winds are not destructive to the fruit.

The fruit is pyriform in shape with a slight depression in the area adjacent the stem. The fruit is classed as medium to large, being in the range of from 20 to 25 ounces. The fruit varies in size from 5 to 6 inches in length and 4 to 4.5 inches in breadth. The skin is medium thin and pliable. However, there are some stone cells. The skin is almost smooth, as seen in the photographs, but has faint rugosity. The skin has a glossy sheen and is medium dark green.

The flesh of the fruit is in the range of pale yellow to cream. It has a thick consistency and a complete lack of fibre. The flavor is excellent. The oil content is from 10 to 15 percent. The skin adheres tightly to the flesh and does not sag, crack or check when the fruit is green or when it is ripe.

The seed is fairly small, round in shape and tight. However, it may be removed from the dissected fruit without damage thereto. The seed is, in general appearance, the same as most avocado seeds and the seed coat adheres tightly to the seed itself so that when removed from the fruit it is not necessary to scrape out the seed coat prior to eating.

The avocado of this invention has proven itself to have a strong tendency to bear consistently and to have a strong tendency to eliminate the strong alternation found in many other varieties.

As well as having lasting qualities upon the tree as heretofore mentioned, this avocado also keeps well after harvesting for long periods thus making it possible to ship for long distances without danger of excessive loss.

I claim as my invention:

1. The variety of avocado substantially as herein disclosed and described, characterized by the vigorous growth of the tree, the size of the fruit, the texture and taste of its flesh, the duration of the harvest season from November to February, and the ability of the tree to hold its fruit in adverse weather conditions.

No references cited.

ROBERT E. BAGWILL, Primary Examiner